(12) United States Patent
Schrijver

(10) Patent No.: US 6,245,035 B1
(45) Date of Patent: Jun. 12, 2001

(54) MEDIUM HEAVY DUTY ANKLE BRACE

(76) Inventor: Floor Schrijver, Oregondreef 5-7, NL-3565 BE Utrecht (NL)

( * ) Notice: Subject to any disclaimer, the term of this patent is extended or adjusted under 35 U.S.C. 154(b) by 0 days.

(21) Appl. No.: 09/341,071

(22) PCT Filed: Jan. 5, 1998

(86) PCT No.: PCT/NL98/00002
§ 371 Date: Jul. 2, 1999
§ 102(e) Date: Jul. 2, 1999

(87) PCT Pub. No.: WO98/29060
PCT Pub. Date: Jul. 9, 1998

(30) Foreign Application Priority Data

Jan. 5, 1997 (NL) .................................................. 1004931

(51) Int. Cl.[7] .............................. A61F 5/00; A61F 13/00
(52) U.S. Cl. ............................................. 602/27; 602/65
(58) Field of Search ........................... 602/5, 6, 7, 23, 602/25, 27, 65; 128/882

(56) References Cited

U.S. PATENT DOCUMENTS

| | | | |
|---|---|---|---|
| 1,205,206 | * 11/1916 | Hofmeister | ................. 36/89 |
| 4,651,726 | * 3/1987 | Holland | ................. 602/65 |
| 5,099,860 | * 3/1992 | Amrein | ............. 602/27 X |
| 5,219,324 | * 6/1993 | Hall | ............. 602/27 X |
| 5,317,820 | * 6/1994 | Bell et al. | ................. 36/89 |
| 5,366,439 | * 11/1994 | Peters | ................. 602/27 |
| 5,778,563 | * 7/1998 | Ahlbaumer | ............. 602/27 X |
| 5,865,778 | * 2/1999 | Johnson | ................. 602/27 |

FOREIGN PATENT DOCUMENTS

2241170 * 8/1991 (GB) ..................................... 602/27

* cited by examiner

*Primary Examiner*—Mickey Yu
*Assistant Examiner*—Denise Pothier
(74) *Attorney, Agent, or Firm*—Michael Best & Friedrich, LLP

(57) ABSTRACT

An ankle brace for a lower leg, ankle and foot of a human having a medial part anatomically adapted to fit the lower leg, the ankle and the foot of a human and a lateral part. The medial part is flexible and includes a sole part adapted to extend beneath the foot. The lateral part is connected to the sole part of the medial part and is substantially more flexible than the medial part.

11 Claims, 1 Drawing Sheet

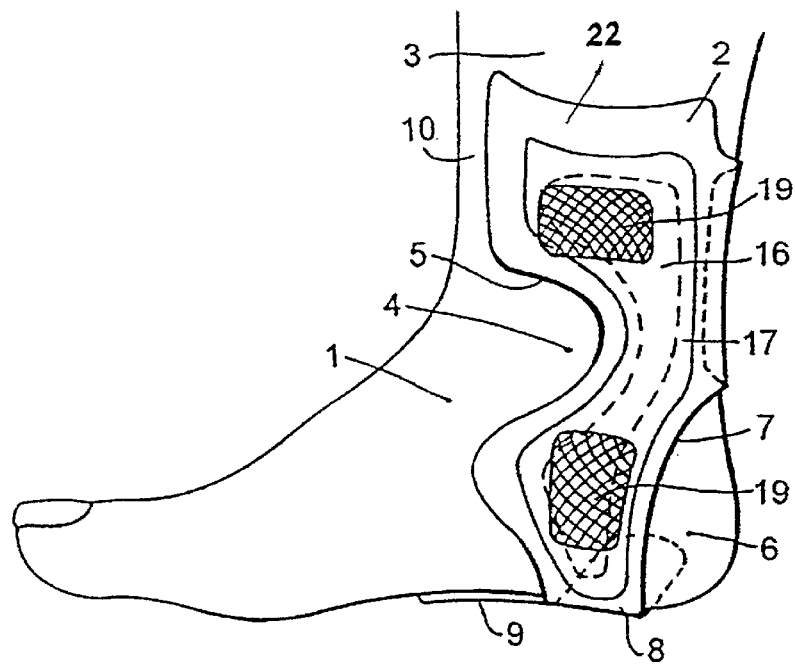
FIG. 1
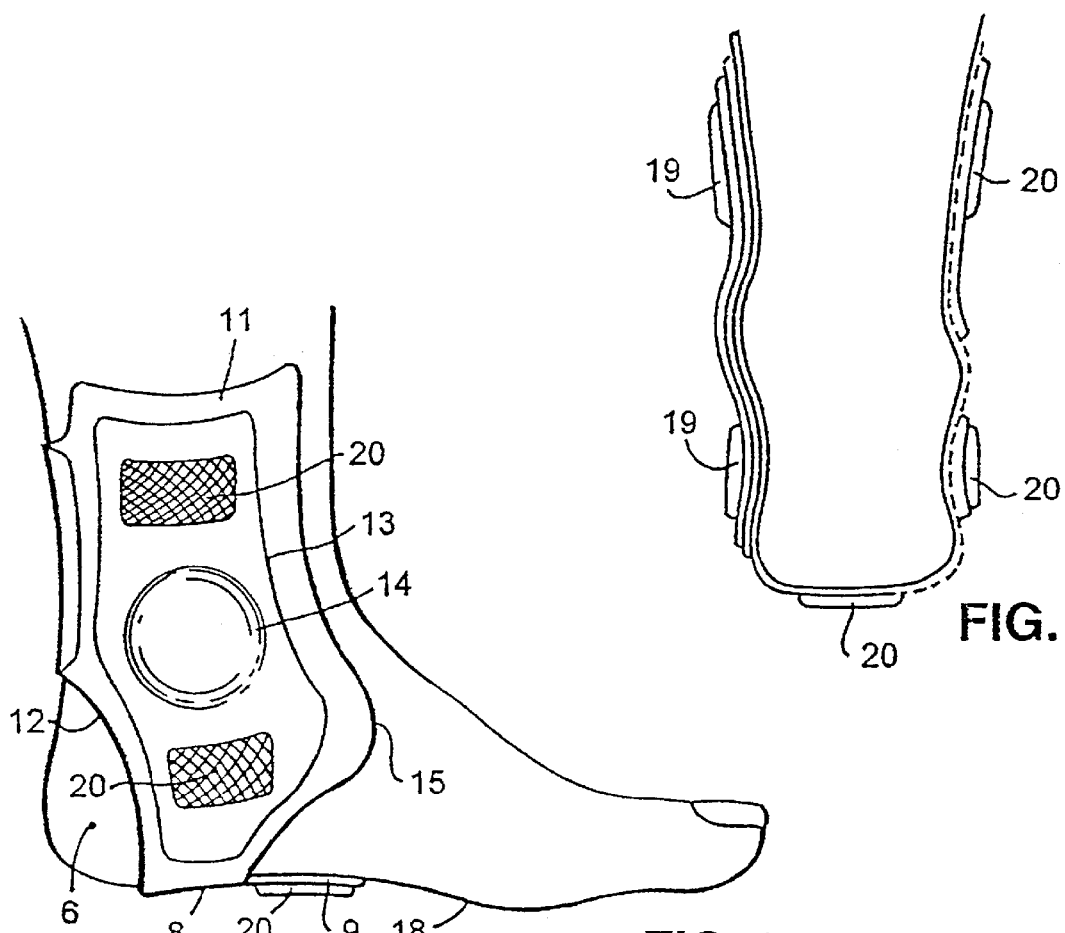
FIG. 2
FIG. 3

MEDIUM HEAVY DUTY ANKLE BRACE

The invention relates to a medium heavy duty ankle brace, which comprises a medial part that is anatomically adapted to the lower leg, the ankle and the footshape, in which the medial part shows a recess at the location adapted to leave the medial ankle joint uncovered and has a substantially flat sole part below the foot, such as known form EP 0 372 452.

In certain cases, such as when the foot has a natural tendency to sprain inwards and/or during sports that give a heavy strain on the ankle, the stability and the protection against spraining inwards of the foot is insufficient. Thereby it is then possible, that the foot sprains inwards, by which so-called inversion traumas can occur in the ankle. These inversion traumas can only heal after an elaborate and long medical and/or physiotherapeutical treatment.

Ankle braces can be divided into light duty, medium heavy duty and heavy duty ankle braces.

At light duty ankle braces, which frequently have the shape of a stocking that has been reinforced with balleens, the stabilisation effect to be expected is practically nil.

Medium heavy duty ankle braces, which allow some freedom of movement to the ankle, are an intermediate shape between light duty and heavy duty ankle braces.

Heavy duty ankle braces, which are mostly provided with a stiff plastic or metal frame, which indeed have a great stabilisation effect, have the objection of a too large limitation of movement because of the stiffness of the material, among others during sport and play. With these heavy duty and stiff ankle braces problems of irritation of the foot and lower leg frequently occur.

There is therefore the need of a medium duty ankle brace, which at the one hand gives enough stability, when the foot has the tendency of spraining inwards. Next to this sufficient stability it is at the other hand of importance, that most normal movements of the foot and leg can take place without irritation.

At the medium heavy duty ankle bracing according to EP 0 372 452 firstly the objection is present, that the stirrup shaped, somewhat flexible ankle brace gives insufficient freedom of movement to the lateral side. Secondly the fastening band cuts over the frontside of the uncovered forefoot, by which damages of the skin can occur.

Thirdly the substantially flat support part has a fixed width, by which no setting for the adaptation of the several foot widths of several users is possible, so that the supplier must keep a larger number of several sizes in stock.

The object of the invention is removing these objections and providing an ankle brace with firstly such a stability, that when a foot has the natural tendency of spraining inwards and also at heavy ankle strains, the danger of spraining inwards of the foot is removed. Secondly so much freedom of movement must remain, that most normal movements of foot and leg can take place without irritation.

Thirdly it should also be possible to adapt as much as possible to the several foot widths of several users.

This object is reached according to the invention, in that the ankle brace is built up from two different asymmetrical shell parts, a substantially flexible medial part with one or more different, local stiffening elements and a lateral part being substantially more elastic than the medial part.

By the application of the invention the substantially flexible medial part gives the necessary differentiated brace to the ankle against spraining inwards, whereas the lateral part, which is substantially more elastic, at the one hand encounters an outward spraining and cooperates with the proper fixation of the ankle brace, but at the other hand allows sufficient freedom of movement and thirdly gives a greater freedom to the adaptation to different foot sizes.

According to a preferential embodiment of the invention the medial part is shaped as a shell, which extends from substantially the middle of the backside of the lower leg to the front side of the lower leg and leaves the front side of the lower leg free, whereas a heel recess extends from the level of the inner ankle joint to the sole, but the sole part extends substantially below the complete heel and below at least a part of the middle foot.

According to another preferential embodiment the lateral part has the shape of a shell of elastic material, which is closely connected to the medial part below the heel and has a heel recess at the backside at the medial side of the heel, whereas the front side is adapted the cover at least a part of the middle foot by means of a projecting rounded part.

The invention will now further be elucidated referring to the accompanying drawing of a preferential embodiment.

FIG. 1 shows a side view on the medial side of an ankle brace according to a preferred embodiment of the invention, which is applied on a left lower leg and foot.

FIG. 2 is a back view with cross section of an ankle brace on a right foot.

FIG. 3 shows a side view on the lateral side of an ankle brace according to a preferred embodiment of the invention shown in FIG. 1.

FIG. 1 shows the ankle brace according to a preferred embodiment of the invention, which comprises, at the medial side (innerside) of the foot, generally indicated with 1, a somewhat stiff, but yet flexible medial part or shell 2, which is anatomically adapted to the lower leg 3, the ankle 4 and the foot shape. Going from above to below: this part or shell 2 extends with the upperpart around the innerside of the left lower leg 3, shows a recess 5 in the middle part at the location of the ankle joint 4, and has a heel recess 7 at the lower part at the backside at the occasion of the heel (generally indicated with 6), and below the heel 6 a substantially flat sole part 8, that has a tongue 9 which extends in a forward direction below the forefoot.

Furthermore the medial part or shell 2 extends from substantially the middle of the backside of the lower leg 3 until a short distance from the middle of the frontside of the lower leg 3 and leaves an open space 10 free at the frontside of the lower leg.

The ankle brace is built up from two different asymmetrical parts, the above somewhat flexible medial part or shell 2 and a more elastic lateral part 11.

The lateral part 11 (outside of the foot) also has the shape of a shell which comprises an elastic material, such as plastic, and extends closely to the solepart 8 of the medial part 2 below the heel 6. The lateral shell 11 has, just as the medial shell 2, a heel recess 12, whereas the frontside covers at least a part of the forefoot with a projecting rounded part 15.

In certain cases the lateral part 11 can comprise at the outside of the elastic shell a more narrow and stiffer stiffening element 13. This stiffening element 13 extends from the upper end of the lower leg part 3 downwards along the heel recess 12 of the lateral shell 11, has a substantially round outer ankle recess 14 and is connected with the medial part or shell 2 below the heel 6, viz. FIG. 2. The lateral part may also comprise more than one stiffening element.

According to a preferential embodiment the medial part or shell 2 is built up from:

a) a lower layer of elastic material, which extends against the lower leg 3 and the foot 18; and b) a more narrow and stiffer stiffening element 16, that extends downwards from the lower leg part between the ankle recess 5 and the heel recess 7 and ends above the sole 8;

c) a broader cover layer 17 that is mounted over the stiffening element 16 and is more flexible than the stiffening element 16, but stiffer than the lower layer 22.

According to another (not shown) embodiment the medial part 2 comprises a second more narrow and stiffer, substantially vertically extending stiffening element on the first stiffening element 16.

According to yet another embodiment the medial part or shell 2 and possibly also the lateral part 11 comprise on the outer cover layer 17, 13 at several locations adhering pieces 19 and 20, for the tag of burring band, with which the ankle brace 2, 11 can be fixed around the ankle and lower foot 18.

In a practical embodiment the medial part or shell 2 and the lateral part 11 are formed with a same underlayer, which is integral. (not shown, known per se)

What is claimed is:

1. An ankle brace for a lower leg, ankle and foot of a human, the lower leg having a front side and a back side, the ankle having a medial ankle joint and the foot having a top side, a bottom side and a heel including a medial side and a lateral side, the ankle brace comprising:

a medial part anatomically adapted to fit the lower leg, the ankle and the foot of a human and completely expose the front side of the lower leg; and a lateral part connected to the sole part of the medial part, the medial part including a sole part adapted to extend beneath the foot and a recess being forwardly open and adapted to substantially expose the medial ankle joint;

a lower layer comprising an elastic material the lower layer being adapted to lie against the lower leg and foot of a human;

a first stiffening element mounted on the lower layer, the stiffening element extending along the lower layer and between the ankle recess and the heel recess;

a cover layer mounted over the first stiffening element, the cover layer being more flexible than the first stiffening element, but less flexible than the lower layer; and a second stiffening element, the second stiffening element being narrower and less flexible than the first stiffening element and being positioned between the first stiffening element and the cover layer.

2. The ankle brace of claim 1, wherein the medial part further comprises one or more local stiffening elements, the medial part being flexible and asymmetric, and the lateral part being asymmetric and substantially more flexible than the medial part.

3. The ankle brace of claim 1, wherein the medial part further comprises a heel recess adapted to expose the medial side of the heel, the medial part being a shell and adapted to extend from substantially a middle of the back side of the lower leg to the front side of the lower leg.

4. The ankle brace of claim 1, wherein the sole part of the medial part extends substantially beneath the heel and at least a portion of the bottom side of the foot.

5. The ankle brace of claim 1, wherein the lateral part further comprises a heel recess adapted to expose the lateral side of the heel, the lateral part being a shell and connected to the sole part of the medial part of the bracing element below the heel when in use.

6. The ankle brace of claim 1, wherein the lateral part of the ankle brace further comprises a substantially elastic lower layer and one or more stiffening elements.

7. The ankle brace of claim 1, wherein the medial and lateral parts of the ankle brace have an integral underlayer.

8. The ankle brace of claim 1, wherein the sole part is substantially flat.

9. The ankle brace of claim 1, wherein the medial part further comprises an outer cover layer and a plurality of adhering pieces mounted on the cover layer, the adhering pieces being mounted such that a burring band can be attached to at least one of the adhering pieces to further fix the ankle brace around the ankle and foot.

10. The ankle brace of claim 1, wherein the lateral part further comprises a plurality of adhering pieces mounted on the lateral part of the ankle brace, the adhering pieces being mounted such that a burring band can be attached to at least one of the adhering pieces to further fix the ankle brace around the ankle and foot.

11. The ankle brace of claim 1, wherein the medial part and the lateral part are separate pieces.

* * * * *